(12) United States Patent
Chen et al.

(10) Patent No.: US 7,241,588 B2
(45) Date of Patent: Jul. 10, 2007

(54) METHOD FOR PRODUCING NOVEL β-LACTAM ANTIBIOTIC FROM PROTOPLAST FUSION STRAIN

(75) Inventors: Chin-Chu Chen, Hsinchu (TW);
Ying-Shih Feng, Taipei (TW);
Charng-Cherng Chyau, Taichung (TW); Ching-Nung Chen, Taoyuan (TW); Shih-Jeng Huang, Changhua (TW); Yen-Lien Chen, Taoyuan (TW); Hung-Ping Tseng, Taoyuan (TW); Wei-Hui Chung, Pingjen (TW); Yi-Hsuan Chen, Dali (TW)

(73) Assignee: Grape King Inc., Jungli, Taoyuan (TW)

( * ) Notice: Subject to any disclaimer, the term of this patent is extended or adjusted under 35 U.S.C. 154(b) by 461 days.

(21) Appl. No.: 10/657,199

(22) Filed: Sep. 9, 2003

(65) Prior Publication Data
US 2005/0054031 A1    Mar. 10, 2005

(51) Int. Cl.
*C12P 37/00*    (2006.01)
*C12P 35/00*    (2006.01)
*C12N 1/00*    (2006.01)

(52) U.S. Cl. .......................................... 435/43; 435/47
(58) Field of Classification Search .................. 435/43, 435/47, 254.11, 254.1, 254.5, 254.3
See application file for complete search history.

(56) References Cited

OTHER PUBLICATIONS

Chang et al. "Protoplast fusion in industrial fungi" Developments Industrial Microbiol. (1982) 23: 21-29.

*Primary Examiner*—Leon B. Lankford
*Assistant Examiner*—Susan Hanley
(74) *Attorney, Agent, or Firm*—WPAT, P.C.; Anthony King

(57) ABSTRACT

The present invention provides a method for producing a novel β-lactam antibiotic from a protoplast fusion strain. The method is to fermentatively culture the protoplast fusion strain of *Penicillium chrysogenum* and *Cephalosporium acremonium*. The ferment filtrate is isolated, lyophilized, and extracted by acetone or acetone/methanol. The extract is concentrated by decompression, and then analyzed by preparation type HPLC to isolate the active antibiotic compound.

4 Claims, 14 Drawing Sheets

6-Aminopenicillanic Acid(6APA)

minocephalosporanic Acid(7ACA)

7-Aminodeacetoxycephalosporanic Acid(7ADCA)

$C_{18}H_{20}O_6N_2S=392$

METHOD FOR PRODUCING NOVEL β-LACTAM ANTIBIOTIC FROM PROTOPLAST FUSION STRAIN

BACKGROUND OF THE INVENTION

1. Field of the Invention

The present invention relates to a method for producing a novel β-lactam antibiotic from a protoplast fusion strain, and more particularly to a method for producing a novel β-lactam antibiotic from a protoplast fusion strain of *Penicillium chrysogenum* and *Cephalosporium acremonium*.

2. Description of the Prior Art

Antibiotics are the most effective drugs for curing bacteria-infectious diseases clinically. They have a wide market for their advantages of strong bactericidal effect, low toxicity and small side effect. Among them, β-lactam antibiotics (mainly penicillin and cephalosporin) are widely used since it has very strong bactericidal effect (by blocking cell division) and very low toxicity. It is estimated that the global sales volume of β-lactam antibiotic is about 21 billion USD in 1999.

Among the β-lactam antibiotics, 210 billion USD is almost contributed from 6-APA (6-amino-penicillinic acid, the intermediate of penicillin, as shown in FIG. 1), 7-ACA (7-amino-cephalosporanic acid, the intermediate of cephalosporin, as shown in FIG. 2), and 7-ADCA (7-amino desacetoxi-cephalosporanic acid, the intermediate of cephalosporin, as shown in FIG. 3). That is, the three aforesaid intermediates predominate above 95% market of β-lactam antibiotics.

However, since the antibiotics have been abused for tens of years, drug-resistant bacteria are rapidly increased. As a result, the current commercially available β-lactam antibiotics, even the first-line antibiotics of their second or third generation, cannot repress the spread of the drug-resistant bacteria, which becomes a serious medical problem. Therefore, it is needed to develop a novel β-lactam antibiotic with small side effect and strong bactericidal effect.

To overcome the problems described above, the present invention provides a method for producing a novel β-lactam antibiotic from a protoplast fusion strain of *Penicillium chrysogenum* and *Cephalosporium acremonium*. That is, the protoplasts of *Penicillium chrysogenum* and *Cephalosporium acremonium* are fused by protoplast fusion to generate a protoplast fusion strain, and a novel β-lactam antibiotic is isolated from this fusion strain. In 1983, Dr. Elander of Brisal Mylc company (Bristal Mylc Squill company now) in USA had tried this method, but he only got the fusion stain, and did not isolate a novel β-lactam antibiotic from the fusion strain (Chang, L. T., Terasaka, D. T. & Elander, R. P. (1982), "Protoplast fusion in industrial fungi", Developments in Industrial Microbiology 23, 21-29; Elander, R. Pin "Overproduction of Microbial Products" (Krumphonal, R., Sikyta, B., and Vanok, Z.), pp353-369, Academic Press, New York (1982)). However, through profound studies for many years, the present inventors obtain the fusion strain of *Penicillium chrysogenum* and *Cephalosporium acremonium*, and isolate the novel β-lactam antibiotic therefrom.

SUMMARY OF THE INVENTION

It is an object of the present invention to provide a method for producing a novel β-lactam antibiotic from a protoplast fusion strain. The method is to fermentatively culture the protoplast fusion strain of *Penicillium chrysogenum* and *Cephalosporium acremonium*. The ferment filtrate is isolated, lyophilized, and extracted by acetone or acetone/methanol. The extract is concentrated by decompression, and then analyzed by preparation type HPLC to isolate the active antibiotic compound.of *Penicillium chrysogenum* and *Cephalosporium acremonium*.

BRIEF DESCRIPTION OF THE DRAWINGS

The drawings disclose an illustrative embodiment of the present invention which serves to exemplify the various advantages and objects hereof, and are as follows.

DETAILED DESCRIPTION OF THE PREFERRED EMBODIMENT

Figure 1:
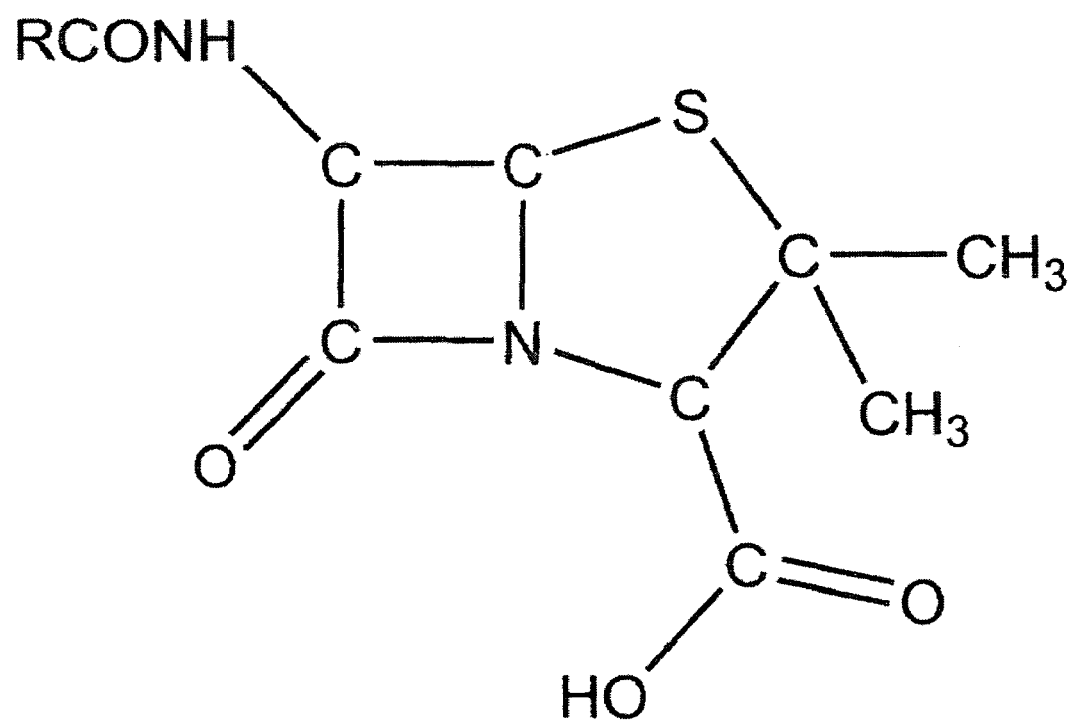
FIG. 1 shows the structural formula and the molecular weight of 6-amino-penicillinic acid.
Figure 2:
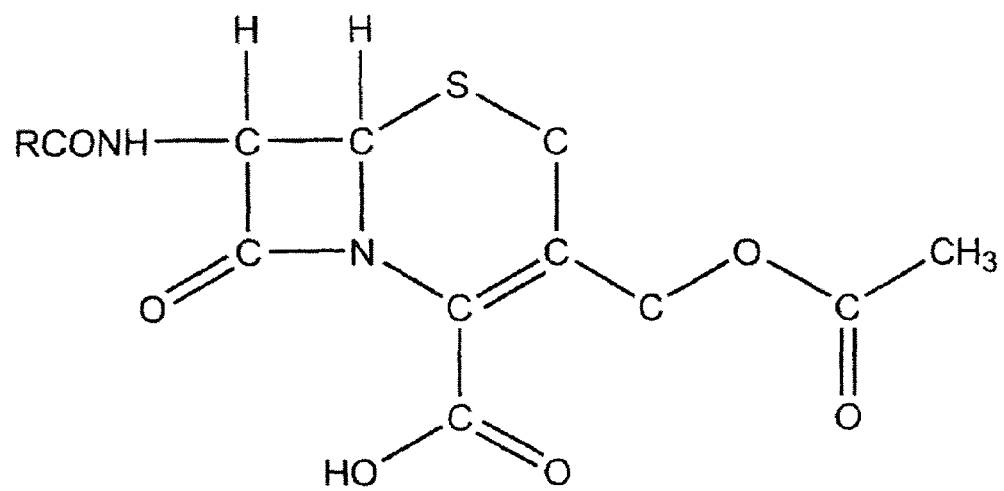
FIG. 2 shows the structural formula and the molecular weight of 7-amino-cephalosporanic acid.
Figure 3:
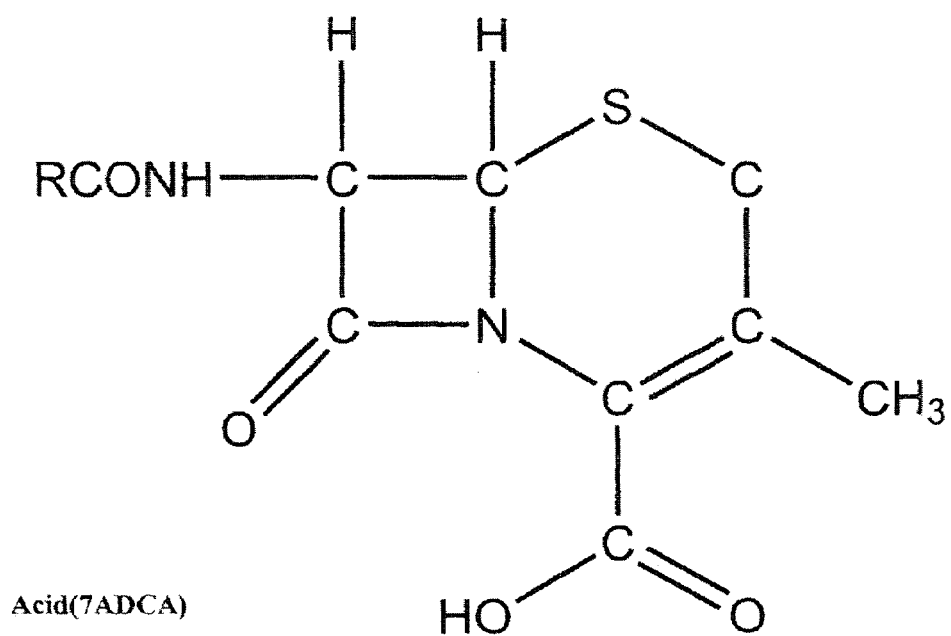
FIG. 3 shows the structural formula and the molecular weight of 7-amino desacetoxi-cephalosporanic acid.

The strain used in the present invention is a fusion strain, which uses drug-resistant mutant stains of *Penicillium chrysogenum* ATCC 48271 (deposited in Food Industry Research Institute, No. CCRC 32181) and *Cephalosporium acremonium* (commercially available from the American Type Culture Collection (ATCC), No. ATCC 48272 as parental strains for protoplast fusion. The cell walls of the two strains are decomposed by enzyme to form protoplasts, according to the method of Patricia et al (Patricia, A Fawceff et al., J. Gen. Microbiol. 79, 293-309, 1973). Then, according to the article, the protoplasts are fused. In brief, the two protoplasts of equal amount (1×106 protoplast/ml) are mixed, centrifuged, and added with polyethyl glycol (PEG, MW =4000-6000). After 5 minutes, the protoplasts are diluted with hypertonic solution, and then cultured on the agar plate at 25° for 4 to 7 days. Finally, selecting the colonies on the plate to obtain the protoplast fusion strain, which was deposited on 27 Sep. 2005 at the Food Industry Research Institute. 331 Shih-Pin Road, Hsinchu, 300 Taiwan R.O.C. as deposition No. EP 020082 and stain No. CCRC930060. The spores of the strain are inoculated on the potato dextrose agar (PDA) plate and cultured at 30° for about a week. Then the hyphas on the plate are scraped and inoculated in the flask, and cultured with the medium described below at about 30° and pH 6.5, on a shaker with a shaking rate of 50-250 rpm, for 5 to 7 days for growing to the initial log phase.

| Component | Amount (weigh %) |
|---|---|
| Sucrose | 12 |
| Lard | 0.1 |

-continued

| Component | Amount (weigh %) |
|---|---|
| Ammonium sulfate | 2 |
| Di-potassium hydrogen phosphate | 0.05 |
| Sodium citrate | 0.4 |
| Phenoxyacetic acid | 1.12 |

Subsequently, the culture in the flask is inoculated in the fermentor, and cultured with the medium described above at 30° C., and under the conditions that the tank pressure is 0.5-1.0 kg/cm$^2$, pH 6.5, the aeration rate is 150 l/min, and the stirring rate is 200 rpm, for about 7 days. A mycelium liquid culture suspension of the protoplast fusion strain of *Penicillium chrysogenum* and *Cephalosporium acremonium*, including the mycelium and the supernatant, is obtained.

The mycelium and the supernatant are separated by centrifugation to isolate the mycelium and the ferment filtrate. Then the ferment filtrate is lyophilized (−40° C., 24 hrs), and the lyophilized product is used to isolate the active substances.

Basically, the active substances are isolated by extracting with an organic solution, and by preparation type chromatography coupled with bacteriostatic test. Finally, the active compounds are determined by spectra analysis.

In a preferred embodiment of the present invention, the lyophilized powder of the ferment filtrate is added with acetone and stirred at room temperature for extraction, and then filtered. The residues are repeatedly treated with the above steps for two times. The filtrates are collected and concentrated by decompression. The concentrate is filtered by a filter membrane of 0.22 μm, and then analyzed by preparation type HPLC using 1% methanol as the mobile phase to obtain an active eluent. The eluent is further concentrated to result in the active substances.

In this preferred embodiment, the product generated from acetone extraction and concentration is additionally analyzed by HPLC using 30% acetonitrile as the mobile phase. The eluent corresponding to the retention time of the third peak in the spectrum is collected and concentrated, and then isolated by preparation type HPLC using 30% methanol as the mobile phase to obtain an active sample.

In another preferred embodiment, the lyophilized powder of the ferment filtrate is added with 70% acetone and 30% methanol and stirred at room temperature for extraction, and then filtered. The residues are repeatedly treated with the above steps for two times. The filtrates are collected and concentrated by decompression. Then the concentrate is analyzed by preparation type HPLC using 30% methanol as the mobile phase. The active eluent is collected and concentrated, and then analyzed by preparation type HPLC using 10% metanol as the mobile phase. The eluent corresponding to the retention time of the first (A) peak in the spectrum is collected and concentrated, and then analyzed by preparation type HPLC using 10% methanol as the mobile phase, which results in an analysis spectrum having five peaks. The five eluents corresponding to the retention time of each of the five peaks in the spectrum are collected and concentrated respectively to obtain the active substances.

In the isolation of the active compound, the activity is determined by the bacteriostatic test and the pitting test. *Alcaligenes faecalis* (AL, CCRC10355) and *Micrococcus luteus* (ML, CCRC10449) are the receptor strains used in the bacteriostatic test. The bacteria cultures of the AL and ML strains are added into the nutrient agar at the melting state (about 40° C.) with the proportion of 1:100, then the agar is mixed and poured into the plates. A sterile disk is put on the plate, and 50 μl of the extracted and purified compounds are dropped on the disk. Then the plate is incubated in the incubator at 30° C. for 30 hours. When observing the result, a clear bacteriostatic ring should be shown if a novel β-lactam antibiotic is existed.

In the pitting test, the β-lactamase, penicillinase and penicillin acylase are dropped on the peripheral of the disk containing the purified compounds on the plate. When observing the result after culturing, an obvious pitting should be shown in the pitting test with the β-lactamase. The compounds are also analyzed by HPLC for comparison, which confirms that the compounds are neither penicillin nor cephalosporin. In addition, the novel compounds are screened by the cutting test of penicillin acylase (a side-chain cutting enzyme). Finally, the screened compound is analyzed to determine the chemical structure thereof.

By speculating the functional groups and the molecular weight by means of IR, NMR and LC-MS, the structural formula of the compound can be determined.

The present invention is described in detail by the following unlimited embodiments.

EXAMPLE 1

Culture of the Protoplast Fusion Strain of *Penicillium chrysogenum* and *Cephalosporium acremonium*:

(1) Mycelium strain: The strain is deposited in Food Industry Research Institute as deposition No. EP 020082 and stain No. CCRC930060.

(2) Plate culture: The spores are inoculated on the PDA plate and cultured at 30° C. for about one week.

(3) Flask culture: The spores and the hyphas on the plate are scraped and inoculated in the flask, and cultured with the medium described below at about 30° C. and pH 6.5, on a shaker with a shaking rate of 50-250 rpm, for 5 to 7 days for growing to the initial log phase.

(4) Medium:

| Component | Amount (weigh %) |
|---|---|
| Sucrose | 12 |
| Lard | 0.1 |
| Ammonium sulfate | 2 |
| Di-potassium hydrogen phosphate | 0.05 |
| Sodium citrate | 0.4 |
| Phenoxyacetic acid | 1.12 |

(5) Fermentor culture: The culture in the flask is inoculated in the fermentor, and cultured with the medium described above at 25° C., and under the conditions that the tank pressure is 0.5-1.0 kg/cm$^2$, pH 6.5, the aeration rate is 150 l/min, and the stirring rate is 200 rpm, for about 7 days. A mycelium liquid culture suspension of the protoplast fusion strain of *Penicillium chrysogenum* and *Cephalosporium acremonium*, including the mycelium and the supernatant, is obtained.

(6) Result: 2 kg mycelium (dry weight) and 90 liter filtrate are obtained from 100 liter ferment solution after fermentation.

EXAMPLE 2

Isolation, extraction and purification of the active substance from the protoplast fusion strain of *Penicillium chrysogenum* and *Cephalosporium acremonium*:

Rough Isolation of the Active Substances:

The mycelium and the supernatant are separated by centrifugation with 3200 rpm (4000×g) using the conventional centrifuge Decater NX418 S of ALFA LAVAL in Sweden, to isolate the mycelium and the ferment filtrate. Then the ferment filtrate is lyophilized (−40° C., 24 hrs), and the lyophilized product is used to isolate the active substances.

Extraction and Purification of the Active Substance:

100 g lyophilized powder of the ferment filtrate is added with 1 liter acetone and stirred (120 rpm) at room temperature for extraction, and then filtered after 12 hours. The residues are repeatedly treated with the above steps for two times. The filtrates are collected and concentrated by decompression (−40° C., 50 mTorr). The concentrate is filtered by a filter membrane of 0.22 μm, and then analyzed by preparation type HPLC (Hitachi with C18 column of 250×4.6 mm, flow rate of 5 ml/min, and a photodiode sensor) using 1% methanol as the mobile phase to result in an analysis spectrum having five peaks. The five eluents corresponding to the retention times of the five peaks in the spectrum is respectively collected and concentrated according to the above-mentioned concentration method, and the resulted samples are named M-1, M-2, M-3, M-4 and M-5.

EXAMPLE 3

Activity analysis of the novel β-lactam antibiotic (bacteriostatic test) and the confirmation of the intermediate (pitting test and HPLC analysis):

Bacteriostatic Test:

*Alcaligenes faecalis* (AL, CCRC10355) and *Micrococcus luteus* (ML, CCRC10449) are the bacteria strains used in the bacteriostatic test. The bacteria cultures of the AL and ML strains are added into the nutrient agar at the melting state (about 40° C.) with the proportion of 1:100, then the agar is mixed and poured into the plates. A sterile disk is put on the plate, and 50 μl of the extracted and purified compounds in Example 2 are dropped on the disk. Then the plate is incubated in the incubator at 30° C. for 30 hours. When observing the result, a clear bacteriostatic ring should be shown if a novel β-lactam antibiotic is existed.

Pitting Test:

The pitting test is proceeded by the same process of the bacteriostatic test. The β-lactamase, penicillinase and penicillin acylase are dropped on the peripheral of the disk containing the purified compounds on the plate. When observing the result after culturing, an obvious pitting should be shown in the pitting test with the β-lactamase. The compounds are also analyzed by HPLC for comparison, which confirms that the compounds are neither penicillin nor cephalosporin. In addition, the novel compounds are screened by the cutting test of penicillin acylase (a side-chain cutting enzyme). As a result, only M-4 is cut. Therefore, M-4 is further analyzed to determine the chemical structure thereof.

EXAMPLE 4

Structural analysis of the intermediate of the novel β-lactam antibiotic:

M-4 compound is analyzed by means of IR, NMR and LC-MS to speculate the functional groups and the molecular weight, and further determine the structural formula of the compound.

Structural analysis of M-4

Figure 4:
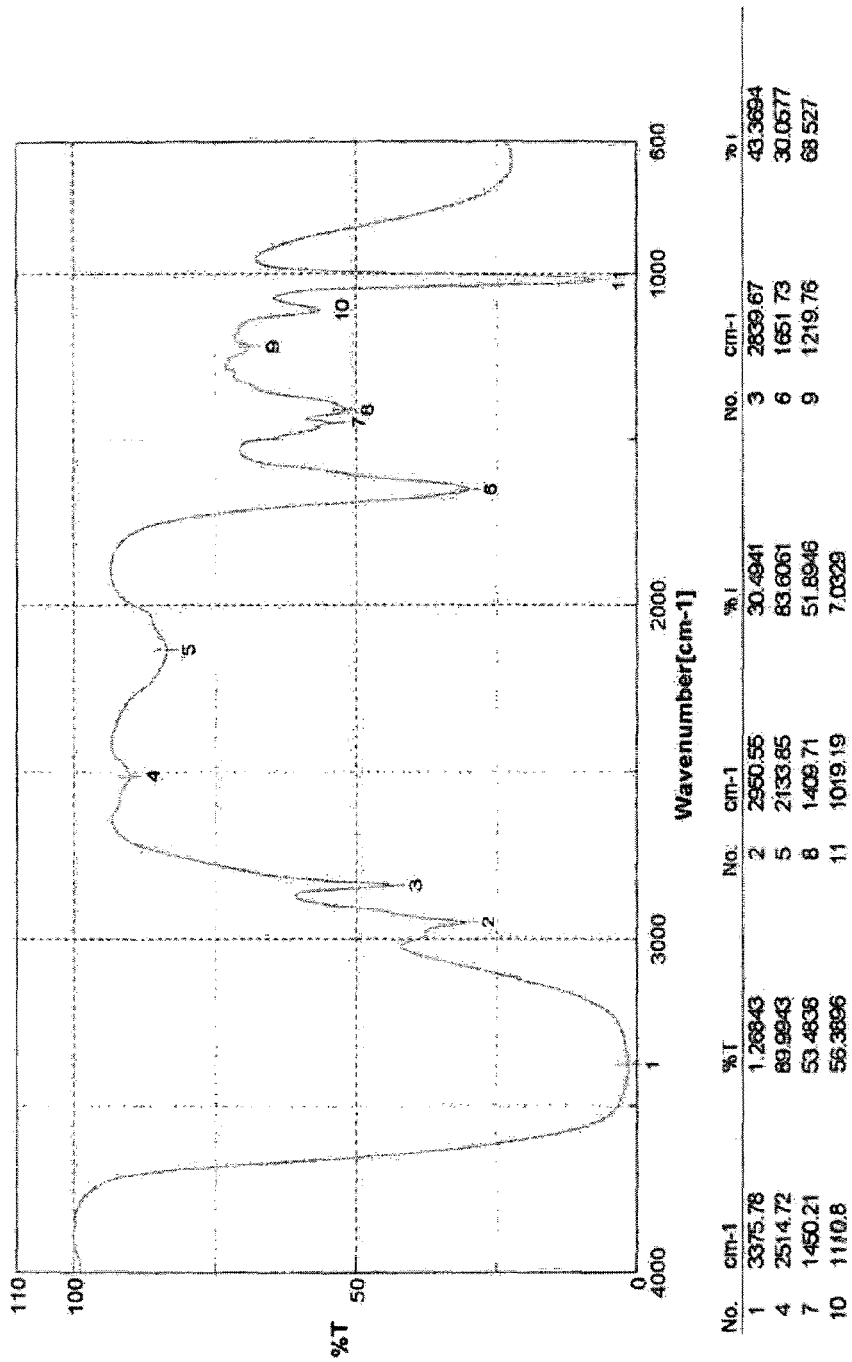
FIG. 4 is the IR spectrum of the compound M-4.

IR: 2950, 2839, 2514, 2133, 1651, 1450, 1409, 1219, 1110, 1019 cm$^{-1}$, as shown in FIG. 4.

Figure 5:
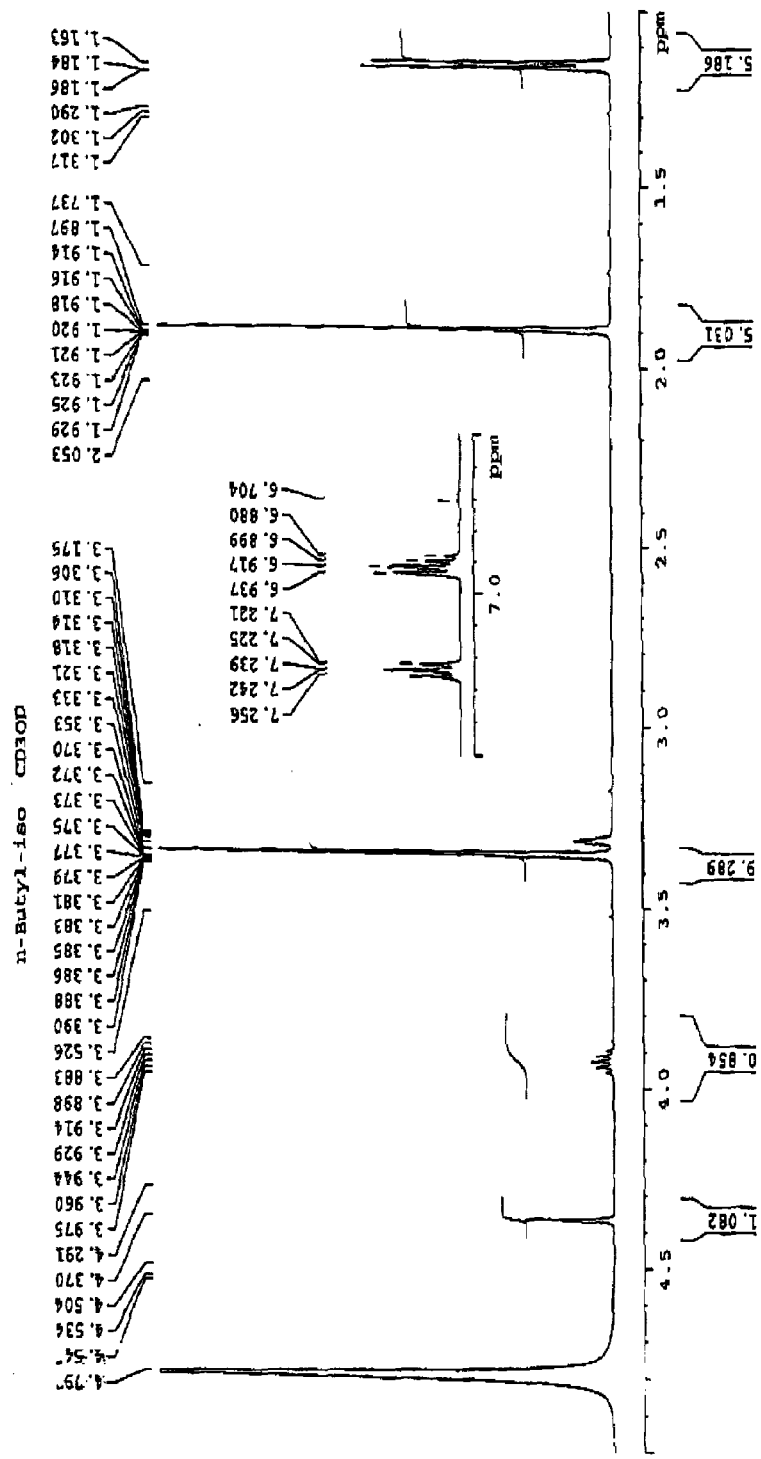
FIG. 5 is the $^1$H-NMR spectrum of the compound M-4.

NMR: as shown in FIG. 5.

Figure 6:
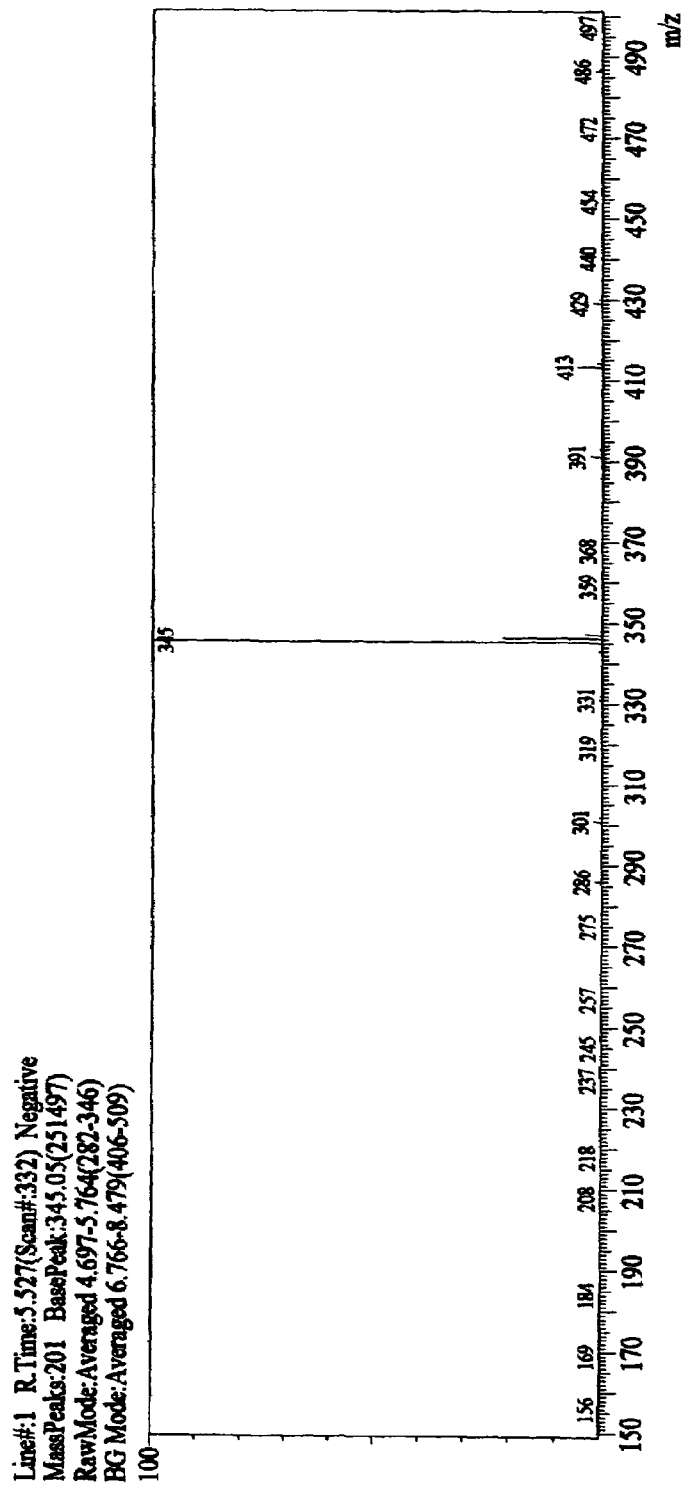
FIG. 6 is the LC-MS spectrum of the compound M-4.

LC-MS: m/z=345, Rt: 5.5, as shown in FIG. 6.

Figure 7:
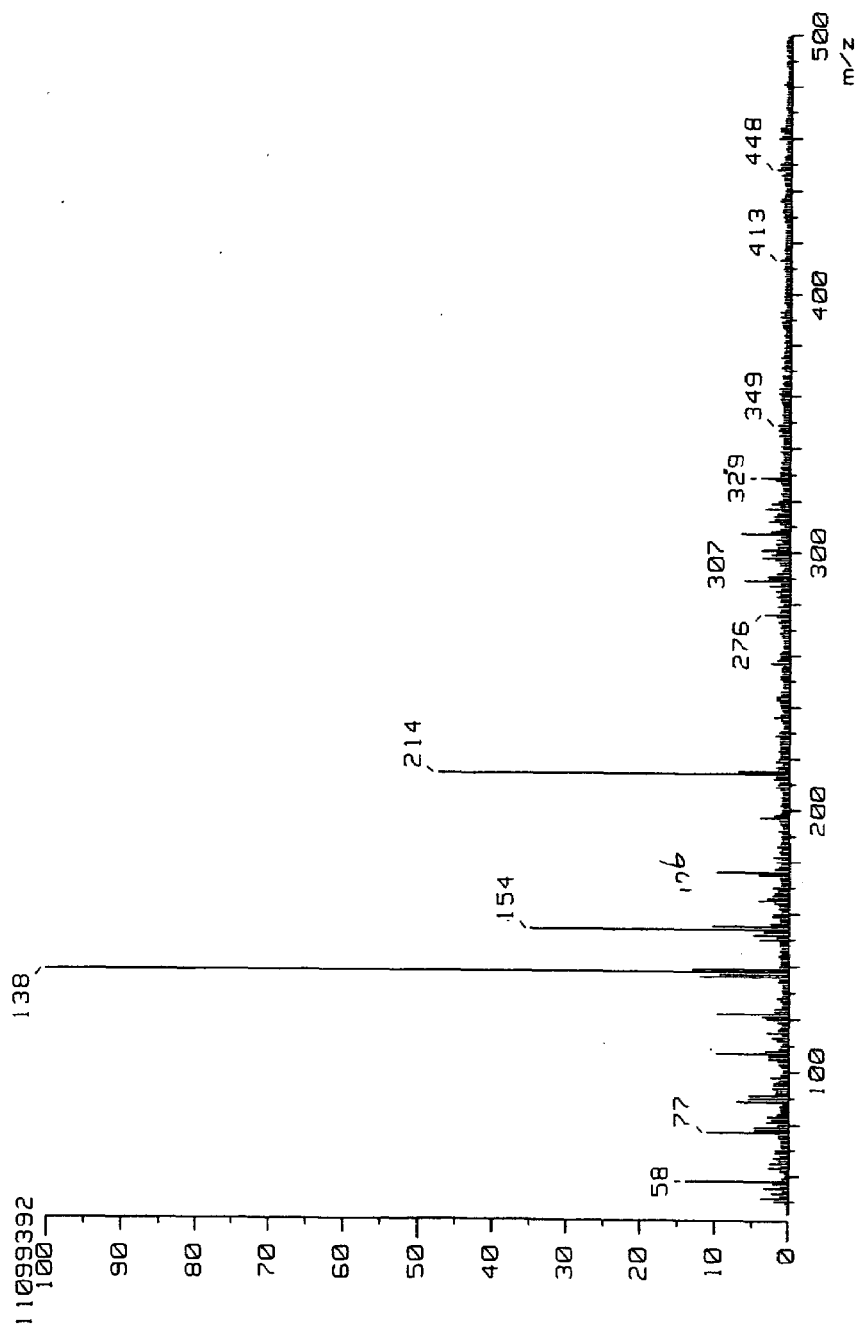
FIG. 7 is the FAB-MS spectrum of the compound M-4.

FAB-MS: [M+1]=349 m/z, as shown in FIG. 7.

Figure 8:
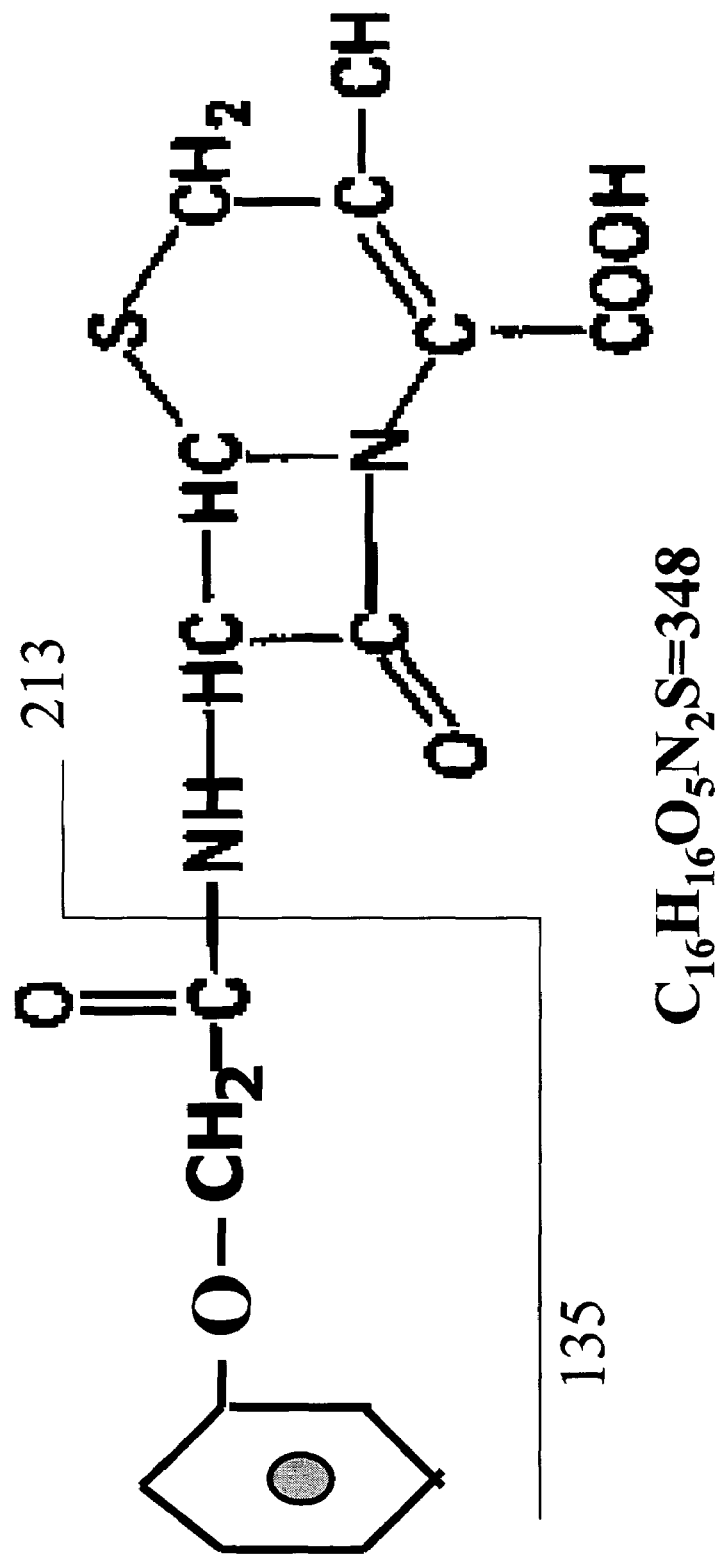
FIG. 8 is the structural formula of the compound M-4.

The structural formula of M-4 is shown in FIG. 8 speculated from the above spectrum analyses.

Structural analysis of A-3-2

Figure 9:
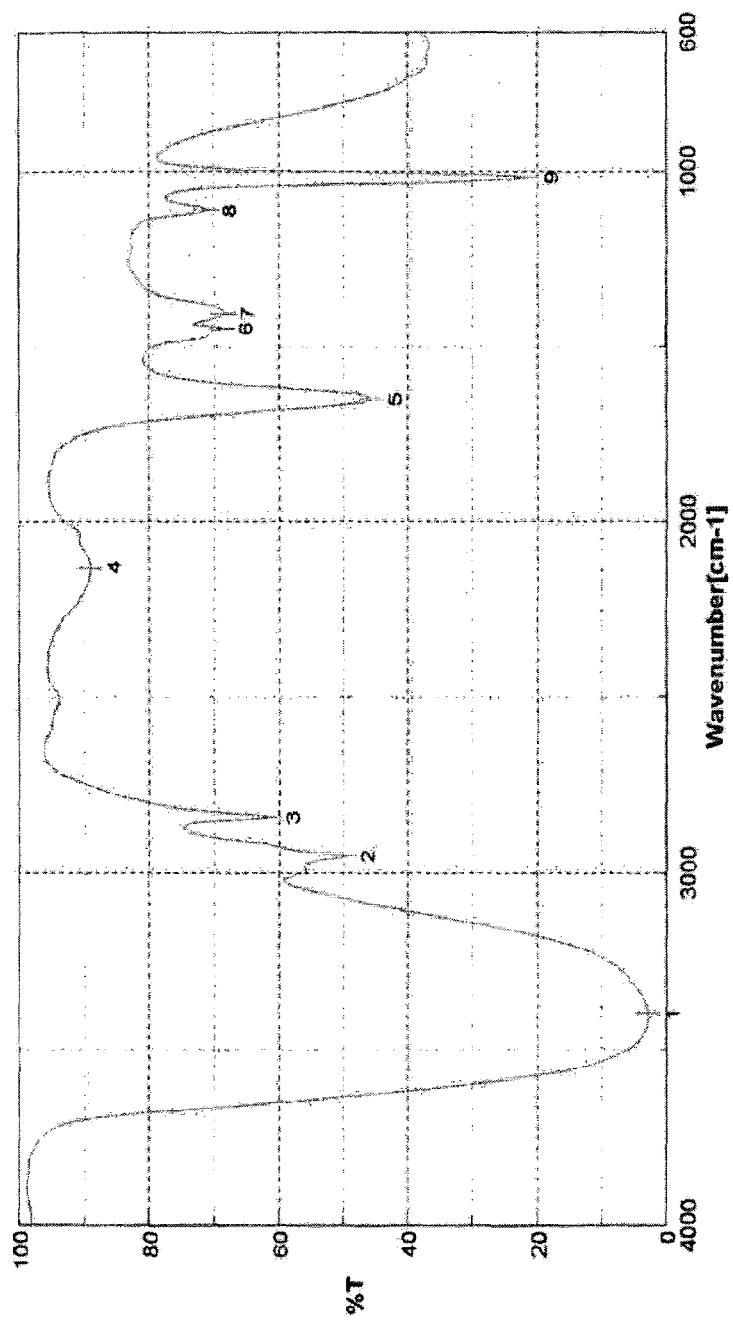
FIG. 9 is the IR spectrum of the compound A-3-2.

IR: 3397, 2951, 2840, 2131, 1650, 1450, 1405, 1110, 1017 cm$^{-1}$, as shown in FIG. 9.

Figure 10:
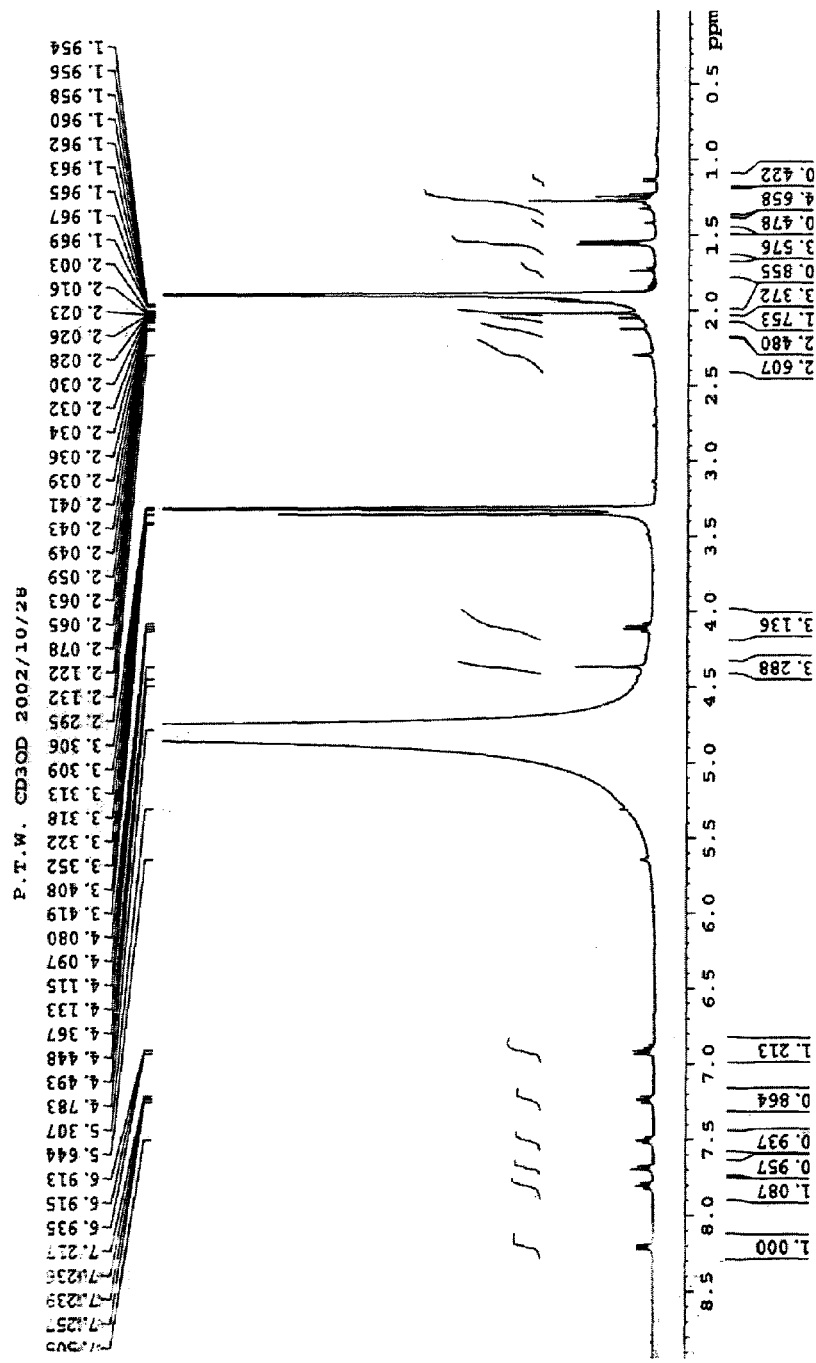
FIG. 10 is the $^1$H-NMR spectrum of the compound A-3-2.

NMR: as shown in FIG. 10.

Figure 11:
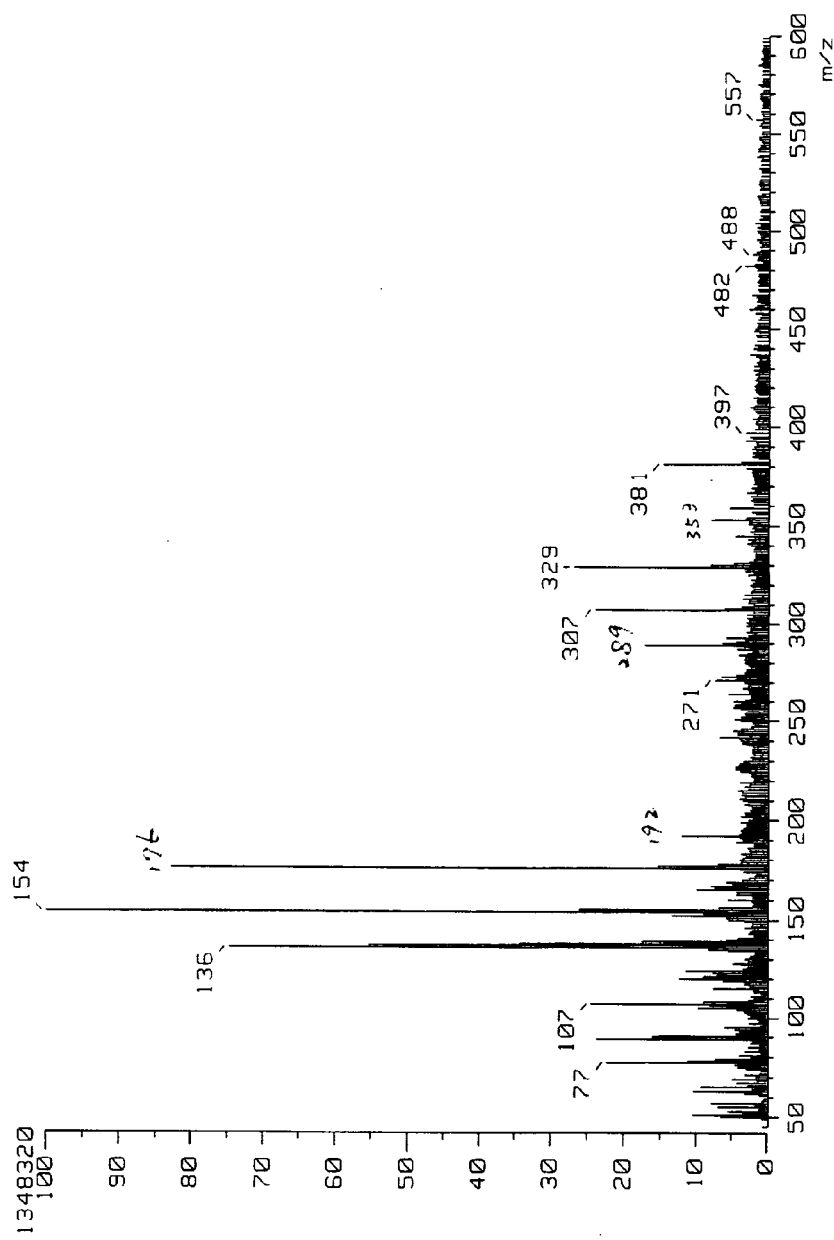
FIG. 11 is the FAB-MS spectrum of the compound A-3-2.

FAB-MS: as shown in FIG. 11.

Figure 12:
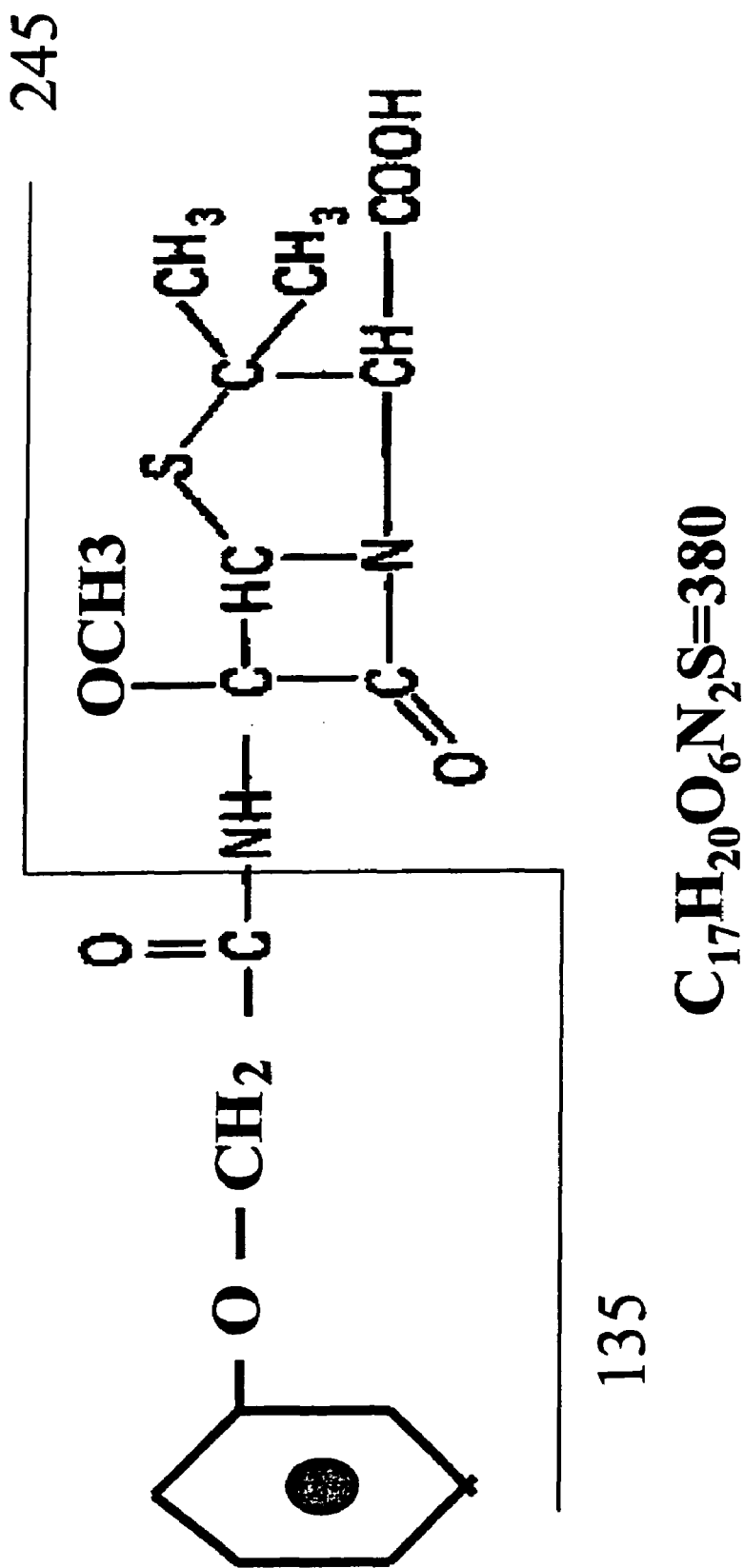
FIG. 12 is the structural formula of the compound A-3-2.

The molecular formula of A-3-2 is $C_{17}H_{20}O_6N_2S$, the molecular weight of A-3-2 is 380, and the structural formula of A-3-2 is shown in FIG. 12, which are speculated from the above spectrum analyses.

Structural analysis of 3-3-A-2

Figure 13:
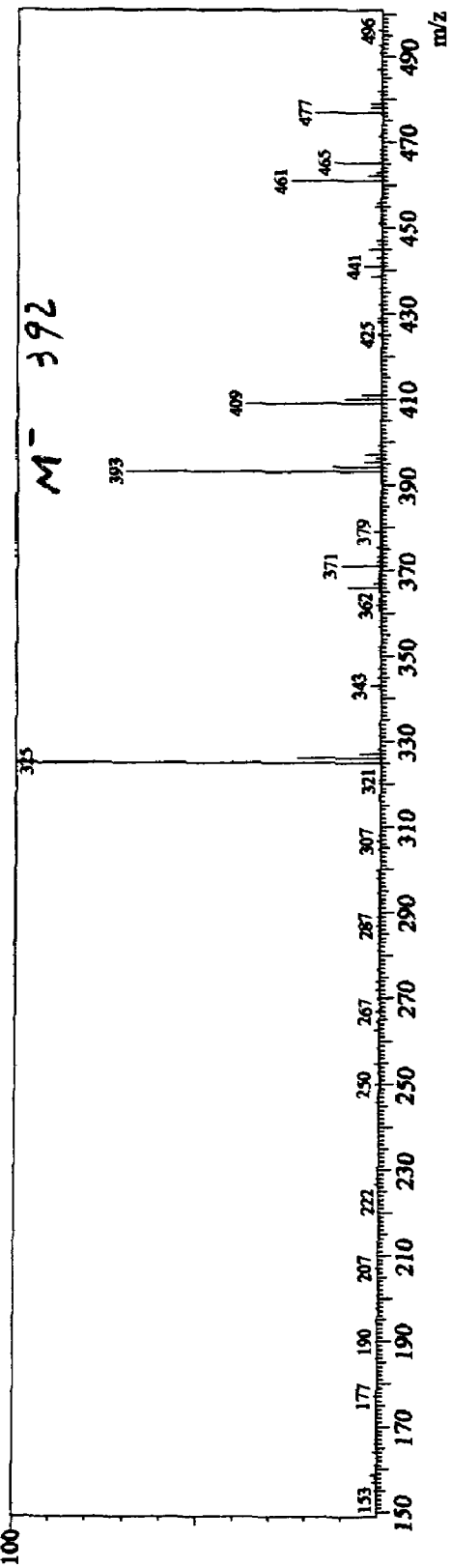
FIG. 13 is the LC-MS spectrum of the compound 3-3-A-2.

LC-MS: as shown in FIG. 13.

Figure 14:
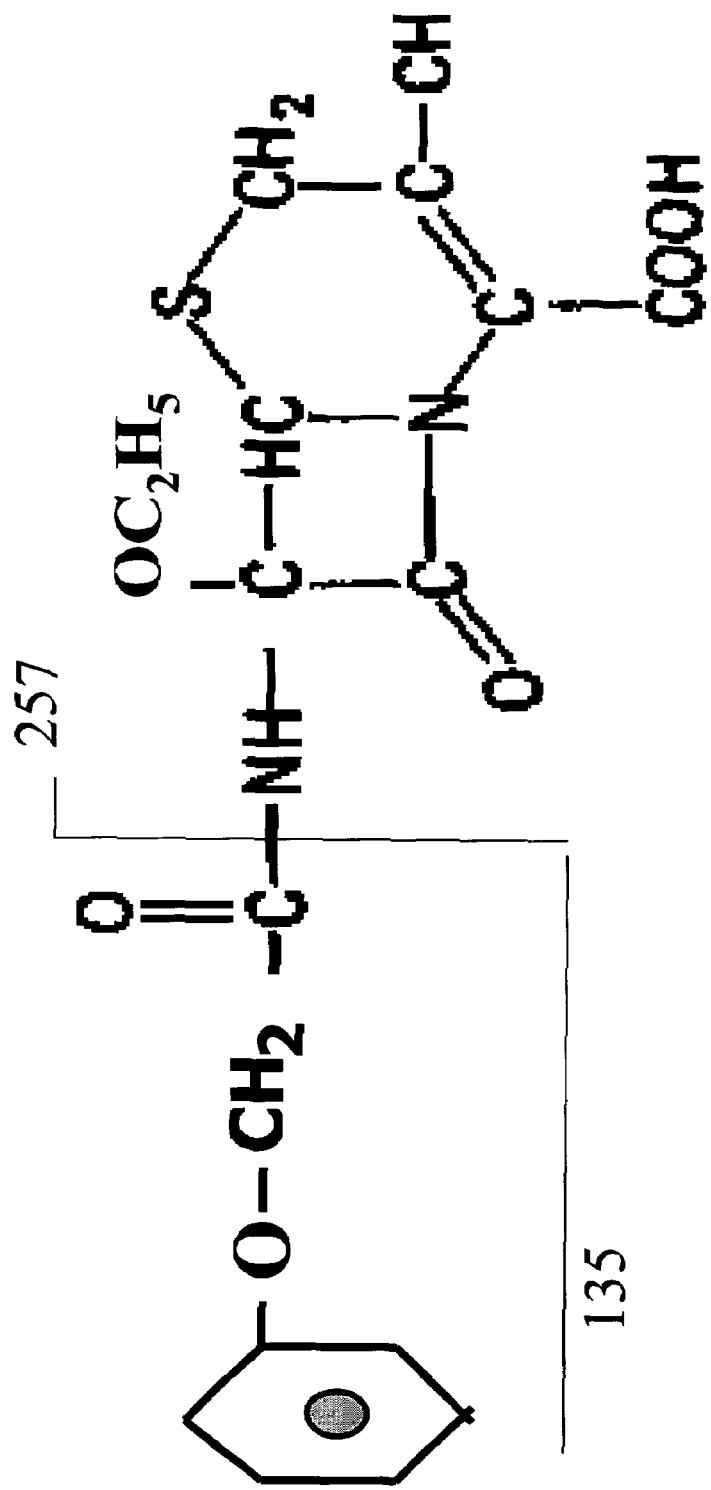
FIG. 14 is the structural formula of the compound 3-3-A-2.

The molecular formula of 3-3-A-2 is $C_{18}H_{20}O_6N_2S$, the molecular weight of 3-3-A-2 is 392, and the structural formula of 3-3-A-2 is shown in FIG. 14, which are speculated from the above spectrum analysis.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for producing a novel β-lactam antibiotic selected from the group consisting of:

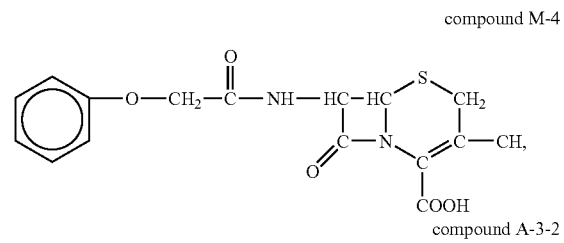

compound M-4

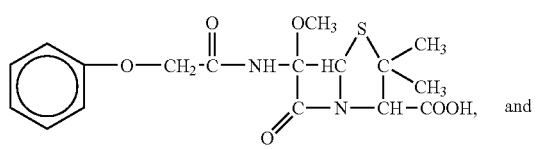

compound A-3-2 and compound 3-3-A-2

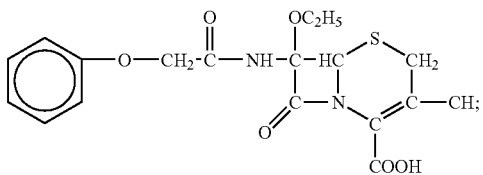

from a protoplast fusion strain CCRC930060, comprising the steps of:

(a) culturing the protoplast fusion strain CCRC930060 which is obtained from the protoplast fusion of *Penicillium chrysogeum* (ATCC 48271) and *Cephalosporium acremonium* (ATCC 48272) with the following medium for fermentative culture:

| Component | Amount (weight %) |
|---|---|
| Sucrose | 12 |
| Lard | 0.1 |
| Ammonium sulfate | 2 |
| Di-potassium hydrogen phosphate | 0.05 |
| Sodium citrate | 0.4 |
| Phenoxyacetic acid | 1.12 | to obtain a liquid culture suspension;

(b) processing said liquid culture suspension of step (a) to obtain a ferment filtrate which is then lyophilized to provide a powder, added with a volume of acetone, stirred at room temperature for extraction, and filtered;

(c) collecting the filtrate obtained in step (b) and concentrating the filtrate by decompression;

(d) filtering the concentrate of step (c) by a filter membrane of 0.22 μm to provide a product;

(e) analyzing the product of step (d) by preparation type HPLC using a mobile phase to obtain an eluent having said antibiotic;

(f) isolating said antibiotic in the eluent obtained in step (e) by a bacteriostatic test and a pitting test; and (g) concentrating the isolated eluent of step (f) to provide said antibiotic.

2. The method according to claim 1, wherein 1% methanol is used as the mobile phase of step (e) to obtain an eluent having compound M4.

3. The method according to claim 1, wherein 30% acetonitrile is as used the mobile phase of step (e) to provide a first eluent comprising compound A-3-2 which is collected, concentrated and then subjected to preparation type HPLC using 30% methanol as the mobile phase to obtain a second eluent comprising compound A-3-2 which then undergoes step (f) of claim 1.

4. The method according to claim 1, wherein in step (b), the lyophilized powder of the ferment filtrate is added with a volume comprising 70% acetone and 30% methanol, stirred at room temperature for extraction, and filtered; and in step (e) wherein 30% methanol is as used the mobile phase for a first preparation type HPLC to provide a first eluent comprising compound 3-3-A-2 which is collected, concentrated, and then subjected to preparation type HPLC using 10% methanol as the mobile phase to obtain a second eluent comprising compound 3-3-A-2 which then undergoes step (f) of claim 1.

* * * * *